(12) United States Patent
Vähäsöyrinki

(10) Patent No.: US 10,828,785 B2
(45) Date of Patent: Nov. 10, 2020

(54) INTEGRATED MEASUREMENT AND MICROMECHANICAL POSITIONING APPARATUS FOR REAL-TIME TEST CONTROL

(71) Applicant: Sensapex Oy, Oulu (FI)

(72) Inventor: Mikko Vähäsöyrinki, Oulu (FI)

(73) Assignee: Sensapex Oy, Oulu (FI)

( * ) Notice: Subject to any disclaimer, the term of this patent is extended or adjusted under 35 U.S.C. 154(b) by 220 days.

(21) Appl. No.: 15/765,608

(22) PCT Filed: Oct. 13, 2015

(86) PCT No.: PCT/FI2015/050688
§ 371 (c)(1),
(2) Date: Apr. 3, 2018

(87) PCT Pub. No.: WO2017/064353
PCT Pub. Date: Apr. 20, 2017

(65) Prior Publication Data
US 2019/0077024 A1   Mar. 14, 2019

(51) Int. Cl.
*G01Q 10/06* (2010.01)
*B25J 13/08* (2006.01)
(Continued)

(52) U.S. Cl.
CPC .............. *B25J 13/085* (2013.01); *B25J 7/00* (2013.01); *B25J 13/087* (2013.01); *B25J 19/023* (2013.01);
(Continued)

(58) Field of Classification Search
CPC ...... G01Q 10/065; B25J 19/023; B25J 13/087
See application file for complete search history.

(56) References Cited

U.S. PATENT DOCUMENTS

| 6,087,743 A * | 7/2000 | Guckel .................. H02K 33/10 310/40 MM |
| 2006/0097727 A1 | 5/2006 | Messenger et al. |

(Continued)

FOREIGN PATENT DOCUMENTS

| EP | 2535151 A1 | 12/2012 |
| JP | 2008271804 A | 11/2008 |

(Continued)

OTHER PUBLICATIONS

Xuemeng Zhang, et al. (Title: Robust Control of a MEMS Probing Device) (Year: 2014).*

(Continued)

*Primary Examiner* — Alvaro E Fortich
(74) *Attorney, Agent, or Firm* — Berggren LLP

(57) ABSTRACT

The invention relates to a measurement device (120), for example for testing, comprising a micromechanical positioning actuator (130) for causing movement of a sensor (150) with respect to a target (110), a positioning controller (145), the positioning controller (145) having an output coupled to the actuator (130) for controlling the movement, and the having an input coupled to the sensor (150) for receiving a sensor signal from the sensor (150) to the positioning controller (145), and the positioning controller (145) arranged to control the movement based on the sensor signal. The measurement device (120) may have memory for storing positioning control instructions (300). The positioning controller (145) may be arranged to control said movement based on said sensor signal and said positioning control instructions (300).

21 Claims, 6 Drawing Sheets

(51) Int. Cl.
  *B25J 7/00*      (2006.01)
  *B25J 19/02*     (2006.01)
  *G01N 33/487*    (2006.01)
  *G01Q 30/14*     (2010.01)
  *B81B 3/00*      (2006.01)
  *G01Q 70/06*     (2010.01)
  *G01Q 60/44*     (2010.01)

(52) U.S. Cl.
  CPC ......... *B81B 3/00* (2013.01); *G01N 33/48728* (2013.01); *G01Q 10/065* (2013.01); *G01Q 30/14* (2013.01); *G01Q 60/44* (2013.01); *G01Q 70/06* (2013.01)

(56) References Cited

U.S. PATENT DOCUMENTS

| | | | | |
|---|---|---|---|---|
| 2007/0125961 | A1* | 6/2007 | Despont | B82Y 35/00 250/492.1 |
| 2008/0223119 | A1* | 9/2008 | Phan | G01Q 10/02 73/105 |
| 2008/0266575 | A1* | 10/2008 | Gaitas | B82Y 35/00 356/600 |
| 2011/0098926 | A1* | 4/2011 | Hwang | G01Q 10/065 701/300 |
| 2012/0042422 | A1* | 2/2012 | Zhou | G01Q 10/06 850/1 |
| 2014/0277712 | A1* | 9/2014 | Vahasoyrinki | B25J 7/00 700/245 |
| 2014/0297222 | A1 | 10/2014 | Shigeno et al. | |
| 2015/0142173 | A1 | 5/2015 | Lewin et al. | |
| 2016/0011231 | A1* | 1/2016 | Shigeno | G01Q 70/04 850/3 |
| 2016/0245843 | A1* | 8/2016 | Shioda | G01Q 70/06 |

FOREIGN PATENT DOCUMENTS

| | | |
|---|---|---|
| JP | 2009208220 A | 9/2009 |
| WO | 2009095720 A2 | 8/2009 |
| WO | 2013068642 A1 | 5/2013 |

OTHER PUBLICATIONS

Zhang X. et al.: "Robust Control of a MEMS Probing Device". IEEE/ASME Transactions on Mechatronics, Feb. 2014, vol. 19, No. 1, pp. 100-108.

European Patent Office, extended European search report of European patent application No. 15906189.4, dated Apr. 17, 2019, 3 pages.

* cited by examiner

INTEGRATED MEASUREMENT AND MICROMECHANICAL POSITIONING APPARATUS FOR REAL-TIME TEST CONTROL

This application is a U.S national application of the international application number PCT/FI2015/050689 filed on 13 Oct., 2015 the contents of which is incorporated herein by reference.

BACKGROUND

Applications involving measuring and controlling electrical and optical signals from micro- and nanometer scale targets are becoming increasingly common. This may involve the use of delicate probes with tip sizes starting from tens of nanometers, which may be positioned relative to the sample in multiple directions with nanometer scale resolution to accurately reach the target. Current technology makes it difficult or impossible to implement test arrangements that require fast control of probe position relative to the target or to implement test arrangements that involve many simultaneous tests or combinations thereof.

There is, therefore, a need for an electrical and/or optical measurement device, which enable more precise control of measurement probe position relative to the target.

SUMMARY

Now there has been invented an improved technical equipment by which the above problems are alleviated. Various aspects of the invention include an apparatus, a system, a method and a computer program product, which are characterized by what is stated in the independent claims. Various embodiments of the invention are disclosed in the dependent claims.

The present application relates to a device for positioning measurement and/or stimulation probe relative to the target in a micromechanical fashion, performing measurements and tests, stimulating or manipulating the target and/or saving measured information in digital format. The device may be an integrated device such that electronics for measurement and/or controlling the micromechanical positioning are embodied in a physically contiguous unit, for example embodied inside a chassis. The application relates to micromechanical positioning and measurement device capable of doing measurements, e.g. electrical and/or optical measurements, and/or stimulation and manipulation and/or various combinations thereof and that is capable of controlling probe position based on the measured information and acquiring, processing, saving and/or transmitting such information in digital format. The positioning apparatus may receive instructions for carrying out positioning based on the measured signals from an external control unit such as a computer. That is, instructions such as script code, computer executable (e.g. binary) code and/or parameters may be received from an external source to the positioning controller so that the positioning controller follows the positioning logic received at least partly from a source external to the positioning controller. This receiving may happen in the set-up phase of the testing or during the testing to provide adaptability to changing conditions.

There is provided a measurement device, comprising a micromechanical positioning actuator for causing movement of one or many probes or sensor(s) with respect to a target, an integrated positioning controller, said positioning controller having an output, said output coupled to said actuator for controlling said movement, said positioning controller having one or many sensor inputs, said sensor input(s) coupled to said one or many sensor(s) for receiving sensor signals from said sensor(s) to said positioning controller, and said positioning controller arranged to control said movement based on said sensor signals.

The measurement device may comprise memory for storing positioning control instructions temporarily or in a non-volatile way, the positioning control instructions comprising computer-readable instructions suitable for use by said positioning controller in controlling said movement based on said sensor signal, and the positioning controller being arranged to control said movement based on said sensor signal and said positioning control instructions. The measurement device may comprise an instruction input for receiving said positioning control instructions to said memory from a source or multiple sources external to said measurement device.

The measurement device may comprise sensor read-out electronics for producing said sensor signal, said sensor read-out electronics being coupled to said sensor and to said sensor input of said positioning controller. The sensor may be an electrical sensor arranged to detect a voltage, current, conductance, capacitance or other electrical characteristics at said sensor, and wherein said sensor read-out electronics comprises a detector and/or an amplifier for detecting or amplifying said electrical characteristics. The amplifier may comprise at least one operational or instrumentation amplifier. The amplifier may have a resistive or capacitive feedback path or a transistor-based feedback path between the output of the operational amplifier and an input of the operational or instrumentation amplifier, or any other structure for realizing amplification or detection of the measured signal. The amplifier may be connected to or it may comprise electronics for preprocessing and/or digitization of the measured signals. The measurement device may comprise a sensor for measuring bioelectric signals, for example a patch-clamp sensor. The sensor may be an optical sensor and said sensor read-out electronics may comprise an optical-to-electric converter coupled to said optical sensor and said sensor input of said positioning controller. The sensor may be a camera and measurement device may comprise an image processor and/or a digital signal processor (DSP). The sensor may comprise a sensor for sensing a physical quantity, for example force sensor, voltage sensor, current sensor or capacitance sensor. The sensor may be a sensor for sensing chemical environment, for example pH level, or any other sensor that is suitable to measure physical signal of interest and convey that information to the integrated positioning apparatus. The measurement device may comprise a plurality of further sensors, at least one micromanipulator actuator for causing movement of at least one further sensor or probe with respect to a target, said positioning controller may have a plurality of further sensor inputs, said further sensor inputs coupled to said further sensors for receiving further sensor signals from said further sensors to said positioning controller, and said positioning controller may be arranged to control said movement based on said further sensor signals. The controlling may be done according to the position control instructions. The measurement device may comprise a current and/or voltage source for controlling voltage of said target and/or injecting current to said target during measurement. The measurement device may comprise a source of electromagnetic radiation for feeding said radiation to said target. The electromagnetic radiation may comprise X-ray radiation and/or visible light, infrared and/or ultraviolet radiation, and/or any radiation suitable for stimulating a living biological target and/or producing fluorescence. The measurement device may also comprise a source of any other type of physical stimulation source that is relevant to specific test, for example to inject liquid or particles to target, to expose target to physical forces, stretching, pushing or pulling or pressure or any other format of physical or chemical stimulation. The positioning actuator, said positioning controller and said sensor read-out electronics may be integrated in a module as a physically contiguous structure. The positioning controller may be arranged to control said movement of said sensor with respect to said target in a closed-loop control such that said sensor signal from said read-out electronics is maintained essentially according to characteristics defined by the instructions (e.g. constant) or movement is stopped at certain condition defined by the instructions.

There is also provided a control unit for controlling a measurement and positioning system, comprising an interface for receiving user input from a user for controlling a measurement, a processor and a memory, computer program code in said memory, said code arranged to, when executed on said processor, cause said control unit to determine positioning control instructions based on said received user input, said positioning control instructions comprising computer-readable instructions suitable for use by a positioning controller of a measurement device in controlling movement of a micromechanical positioning actuator based on a sensor signal, and an instruction interface for providing said positioning control instructions to at least one measurement device of said measurement and positioning system.

There is also provided a measurement system comprising a plurality of devices as described above and a control unit coupled to one or more of said plurality of devices for providing positioning control instructions to said one or more of said plurality of devices.

There is also provided a method for controlling a measurement device, comprising receiving a sensor signal from said sensor to sensor read-out electronics, providing a sensor input to a positioning controller from said read-out electronics based on said sensor signal, said positioning controller and said read-out electronics being integrated in a module as a contiguous structure, and based on said sensor input, controlling a movement of a micromechanical positioning actuator causing movement of a sensor with respect to a target.

The method may comprise receiving positioning control instructions from a source external to said measurement device, said positioning control instructions comprising computer-readable instructions suitable for use by said positioning controller in controlling said movement based on said sensor signal, storing said positioning control instructions in a memory, and controlling said movement based on said sensor signal and said positioning control instructions. Additionally, the instructions may comprise code and/or parameters for manipulating and/or stimulating the target, for example for injecting electric current or applying a voltage, or stimulating the target with light.

There is also provided a computer program product embodied on a non-transitory computer-readable medium, said computer program product comprising positioning control instructions that, when operated on by a processor such as a positioning controller, cause a micromechanical positioning device to receive a sensor signal as an input to a positioning controller, control a movement of a micromechanical positioning actuator, causing movement of a sensor with respect to a target, by using said positioning control instructions in determining said movement based on said sensor signal.

There is also provided a computer program product embodied on a non-transitory computer-readable medium, said computer program product comprising computer code that, when operated on by a processor, cause a control unit of a measurement and positioning system to receive user input from a user for controlling a measurement, determine positioning control instructions based on said received user input, said positioning control instructions comprising computer-readable instructions suitable for use by a positioning controller of a measurement device in controlling movement of a micromechanical positioning actuator based on a sensor signal, and provide said positioning control instructions to at least one measurement device of said measurement and positioning system.

DESCRIPTION OF THE DRAWINGS

In the following, various embodiments of the invention will be described in more detail with reference to the appended drawings, in which.

DESCRIPTION OF EXAMPLE EMBODIMENTS

Figure 1A:
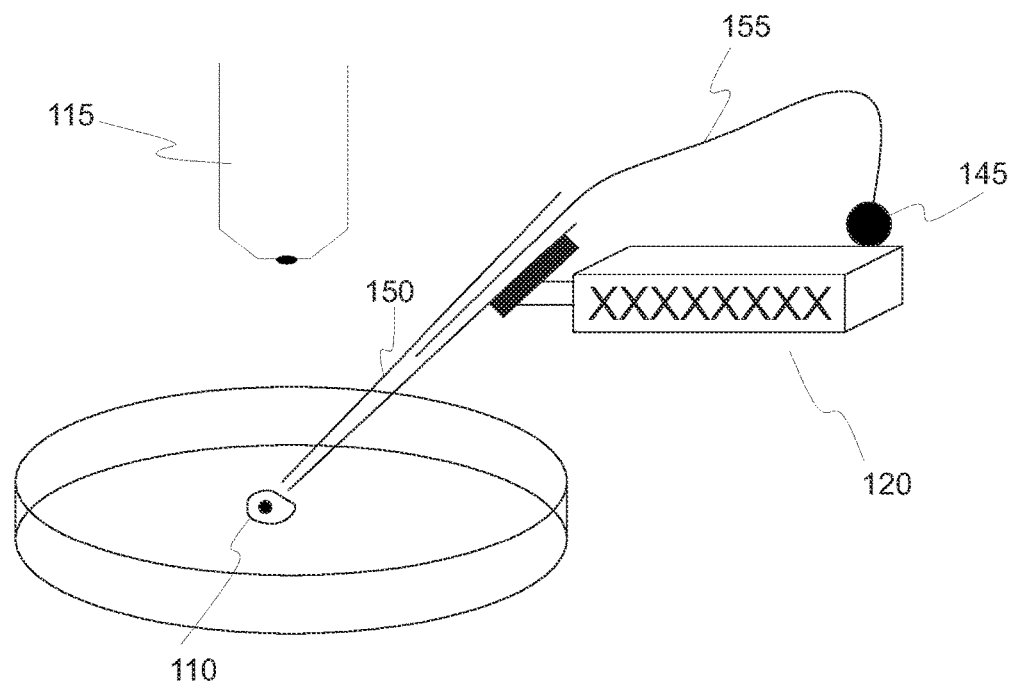
FIGS. 1a and 1b
show an example of electrical measurement from cell in micromechanical manner.

In the following, several embodiments of the invention will be described in the context of micromechanical manipulation. It is to be noted, however, that the invention is not limited to the presented examples. In fact, the different embodiments may have applications in any environment where accurate and fast positioning of a measurement sensor is required.

The invention may in the following be also described in the context of electrical and/or optical measurements that are performed using sensor(s) that are positioned related to the target(s) in micromechanical fashion, where test arrangement involves simultaneously implementing many tests or using measured information to control test in closed-loop manner. It is to be noted, however, that the invention is not limited to examples described here. In fact, the different examples may have applications widely in any environment, where precise measurements of any kind are made based on moving probes and/or sample in micromechanical fashion.

The disclosed measurement device may be used in electrical measurements of biological signals from living cells while controlling their properties through electrical and/or optical stimulation. This may involve use of sensor probes with tip sizes starting from tens of nanometers, which may be positioned relative to the sample in multiple directions with nanometer scale resolution to accurately reach target. Positioning in the range of nanometers, tens or hundreds of nanometers, micrometers and tens or hundreds of micrometers, or in the range of millimeters may be understood to be micromechanical positioning. After reaching the target, the probes may be able to stay in the same position during the measurements and thus mechanical vibrations or drifting of the position may not cause problems. In addition to biological measurements there are also many similar applications in technical fields such as probe stations in failure analysis. It is also often necessary to simultaneously perform many measurements or tests, which involves simultaneous use of a plurality of probes, positioning units and electrical and/or optical measurement or stimulation units. It is also typical that tests need to be automated, which may mean that probes need to be moved relative to the target automatically, for example in a scanning fashion covering a certain space or surface, or to go through certain measurement targets in a sequence (like microcircuits). The measurements and/or stimulation may also be automatically controlled, that is, the test sequence or sequence of measurements may be automatically carried out according to instructions (logic and/or parameters) received from a control unit.

In some applications, finding the optimal measurement position may benefit from fine tuning the probe position based on measured electrical and/or optical or chemical signals in closed-loop manner as presented here. For example, the sensor probe may be moved until a certain measured voltage is detected. Further on, because small samples may be monitored with special equipment such as microscopes with special environmental control chambers, there often is very limited space available to implement all required instrumentation. Small size of a measurement device may also enable close-up installation, which enables using short probes and thus minimizes mechanical lever arms for environmental or user induced vibrations, and minimizes thermal drifts in position. As disclosed here, implementing complex tests and measurements efficiently may benefit from integrating all the instrumentation physically and/or electronically in such a way that information gathered and processed during the tests is available for real-time automated control and data is also saved synchronously in digital format to a memory.

It has been noticed in the present invention that earlier solutions for performing tests and measurements involving multiple electrical and/or optical measurements from micro- and nanometer scale targets using probes that are positioned in micromechanical fashion do not fulfil these needs completely. Currently such test systems are implemented using separate electrical and/or optical measurement apparatuses, which are connected to their separate control boxes, which then connect to a separate data acquisition system. The data acquisition system is in turn then typically connected to computer, which further on connects to separate positioning apparatus control box, which finally sends command to positioning apparatus to move probe based on measured information. Such complex systems are difficult and expensive to build and operating them requires special skills. It has been noticed here that the performance of earlier systems for positioning is not satisfactory because of the associated delays between separate apparatuses, which are typically connected to each other, for example, through slow serial communication interfaces. It has been noticed here that another disadvantage is that such systems become too large in size to fit inside limited space available in the test environment. Therefore, it may not be physically possible, for example, to implement simultaneous measurements with many probes. It has been noticed here that the large size of the system also means long mechanical lever arms in the system, which reduces mechanical stability and exposes the system to thermal drifts. It has also been noticed that the earlier solutions seem to be prone to high noise and thus low quality of measured information.

Figure 1B:
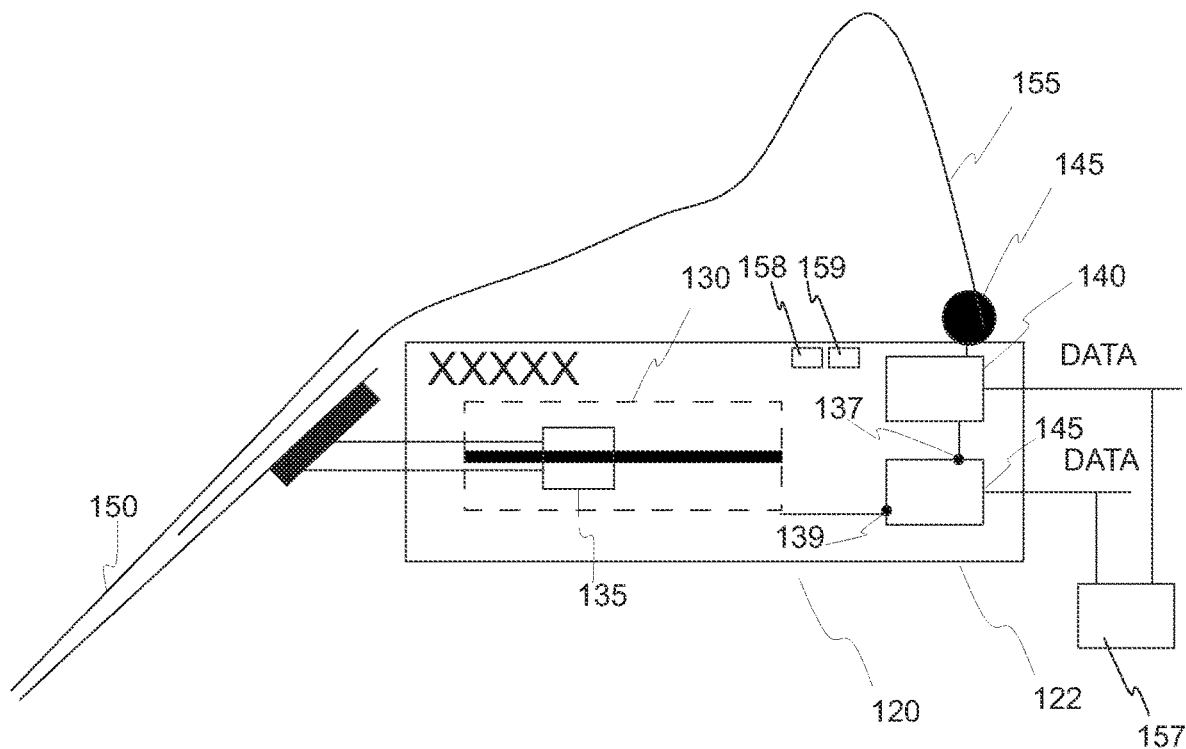

FIGS. 1a and 1b show an example of a measurement device 120 which comprises a micromechanical positioning actuator 130 for causing movement of a sensor 150 with respect to a target 110. A positioning controller 145 is coupled to the actuator 130 for controlling the movement of the sensor 150. The positioning controller 145 has an output which is coupled to the actuator 130 through an interface 139 for controlling the movement of the sensor 150. The positioning controller 145 has an input which is coupled to the sensor 150 for receiving a sensor signal from the sensor to the positioning controller 145. The positioning controller 145 is arranged to control the movement of the sensor 150 based on the sensor signal.

FIGS. 1a and 1b show an example of electrical measurement from a living tissue (living cell) 110 in micromechanical manner. The measurement device 120, i.e. a positioning apparatus, may move the sensor 150, and the target 110 may be observed e.g. using microscope 115. The measurement device 120 comprises read-out electronics 140 for producing a sensor signal. The read-out electronics 140 may be connected to the measurement sensor 150 through an interface 145 and an electrical lead and to the input of the positioning controller 145 through an interface 137.

The read-out electronics 140 may be capable to measure analogue or digital electrical signals and send measured signal digitally to an external computer 157, or to microcontroller 158 or processor 159 that is located in the measurement device 120. Furthermore, information on position and positioning control may be sent as data to an external computer 157, to microcontroller 158 or processor 159, for example for recording. Alternatively the electrical signal may be converted to be suitable for transferring in analogue format to measurement device 120 for AD conversion before transmitting to the microcontroller or processor (FIG. 1b). The measurement device 120 may comprise the positioning controller 145 to electronically control the sensor position with micro- to nanometer resolution (or finer) using electronically controlled actuator 130, which may comprise motors such as stepper motors, servo motors or piezo motors. This control may be done automatically based on measured information, and instructions previously received to the controller may be used in controlling. Said positioning control instructions in the form of executable computer code, script code and/or parameters may be received from an external control unit or computer, which is connected to the apparatus for example using Ethernet. The positioning controller may then follow the positioning logic received at least partly from a source external to the positioning controller (some of the control logic and parameters may already exist on the device). This receiving may happen in the set-up phase of the testing or during the testing to provide adaptability to changing conditions. The measurement device 120 may include means to save and process data and/or transmit it forward to controller or computer or internet.

The measurement device 120 may comprise an enclosure, body or another contiguous structure 122. The positioning controller 145 and the read-out electronics may be embodied within this continuous structure. For example, the different components may be built on the same circuit board or microcircuit. The actuator 130 may be built as part of the continuous structure, or partly outside it, or completely outside.

The sensor 150 may be an electrical sensor arranged to detect a voltage and/or current at the sensor. The sensor read-out electronics 140 may comprise an amplifier for amplifying the detected voltage and/or current. The amplifier may comprise at least one operational or instrumentation amplifier and a transistor-based or resistive or capacitive feedback path between the output of the operational amplifier and an input of the operational amplifier.

A sensor may also comprise capability of measuring capacitance or conductance by employing a bias signal (DC bias for conductance/resistance and AC bias for capacitance). A contact to a metal or semiconductor surface may be detected by resistance measurement without the need of an amplifier by using a signal level detector. In a similar manner, liquid level where biological sample is embedded in may be detected. This detection may be used in controlling the positioning.

Alternatively or in addition, the measurement device 120 may comprise a sensor for measuring bioelectric signals, for example a patch-clamp sensor, or a force sensor, or a sensor for sensing chemical environment, for example pH level.

Alternatively or in addition, the sensor 150 may be an optical sensor, and the sensor read-out electronics 140 may comprise an optical-to-electric converter coupled to the optical sensor and to the input of the positioning controller 145. The optical sensor and the read-out electronics may be arranged to detect intensity, wavelength (spectrum), polarization or any other property of light (electromagnetic radiation in general). The measurement device 120 may comprise an image processor, where the image processor may perform pattern recognition and/or other image processing tasks and produce a signal to the positioning controller. The optical sensor may also be embodied on the same circuit with the positioning controller. For example, in cases when the bandwidth of the electronic communication bus between the read-out electronics and the positioning controller would be a bottleneck, a direct optical fibre connection of light to be measured to the controller may alleviate this problem.

The sensor 150 may be positioned first manually using electronic positioning controller 145 by observing the target 110 and sensor 150 with increasingly large magnifications when approaching the target 110. Electrical signal may be measured during the positioning and a final approach may be done manually or automatically based on the characteristics of the measured signals such as change in the voltage level or sensor impedance as defined in the positioning control instructions. When a good contact between the sensor 150 and test target 110 is achieved many automated measurements may be made while stimulating the test target 110 electrically for example measuring voltage while injecting current pulses or controlling voltage with pulse protocols and measuring currents. Good test condition may be maintained by fine tuning the sensor position based on monitored electrical characteristics for example if the target 110 is slightly moving or deforming, which may happen for example when doing tests with living cells or samples.

The measurement device may have integrated means to measure electrical and/or optical signals and use information from those signals for closed-loop positioning. It may also acquire and process and/or save and/or transfer measured data forward that includes electrical and/or signal and positioning information, i.e. relative timing of different information may be acquired with high precision and provided as part of the measurement data and provided over a computer interface e.g. to a control unit.

The measurement and positioning devices may be able to acquire multiple different measurement signals in parallel, e.g. resistance and capacitance against probes or against target substrate or combination of them. As well as measuring many signals of the same modality simultaneously using many sensors/channels, parallel measurements of different modalities may also be done.

Electronically controlled measurement device may comprise one or more degrees of freedom of movement that can be linear or rotation or whatever kind of movement.

The actuator 130 may comprise one or more moving elements 135. The moving elements may be arranged to be moving e.g. by a piezoelectric drive, or by employing a stepper motor, or any other type of drive that is suitable for micromechanical positioning. Such actuators suitable for micromechanical positioning may be integrated or functionally connected to other equipment. For example, the actuator may be connected to a microscope or may be part of a microscope.

The actuator 130 may have high precision capability for the micromechanical positioning and, for example, the positioning resolution may be 1-10 nanometers or even less than nanometer or few tens of nanometers, and repeatability of the positioning may be 1-10 nanometers, few tens or hundreds of nanometers or between micrometer and few tens of micrometers. Such high precision positioning applications may not tolerate inaccuracies and drift in the position over time may need to be less than few hundred of nanometers per hour or even less or less than few micrometers. The optical/electrical measurement units 140 may have high precision and, for example, the voltage measurement resolution may be 1-10 microvolts or even in nanovolt range or in the range of millivolts and current measurement resolution few picoamperes or even in femtoampere range or in the range or nano and milliamperes. Noise in the high precision electrical measurements may be small and may not exceed microvolts or even less or few hundred of microvolts (peak-to-peak or root-mean-square), or less than few or few hundred of picoamperes or even less than picoampere. For high precision optical measurements the resolution may be at single photon level and noise may need to be also this small, or the resolution and noise requirement may be few tens, hundreds, thousands or even larger number of photons from very short time periods to seconds. The stimulation precision requirements may be at the similar level as the measurement and positioning requirements. The positioning controller 145 may be able to operate with low latency and high synchrony with the measurement unit 140, for example latency may be 1-10 microseconds or even less, a few tens or hundreds of microseconds or a few milliseconds in comparison to conventional solutions where latencies are typically a few tens of milliseconds or more.

Figure 2:
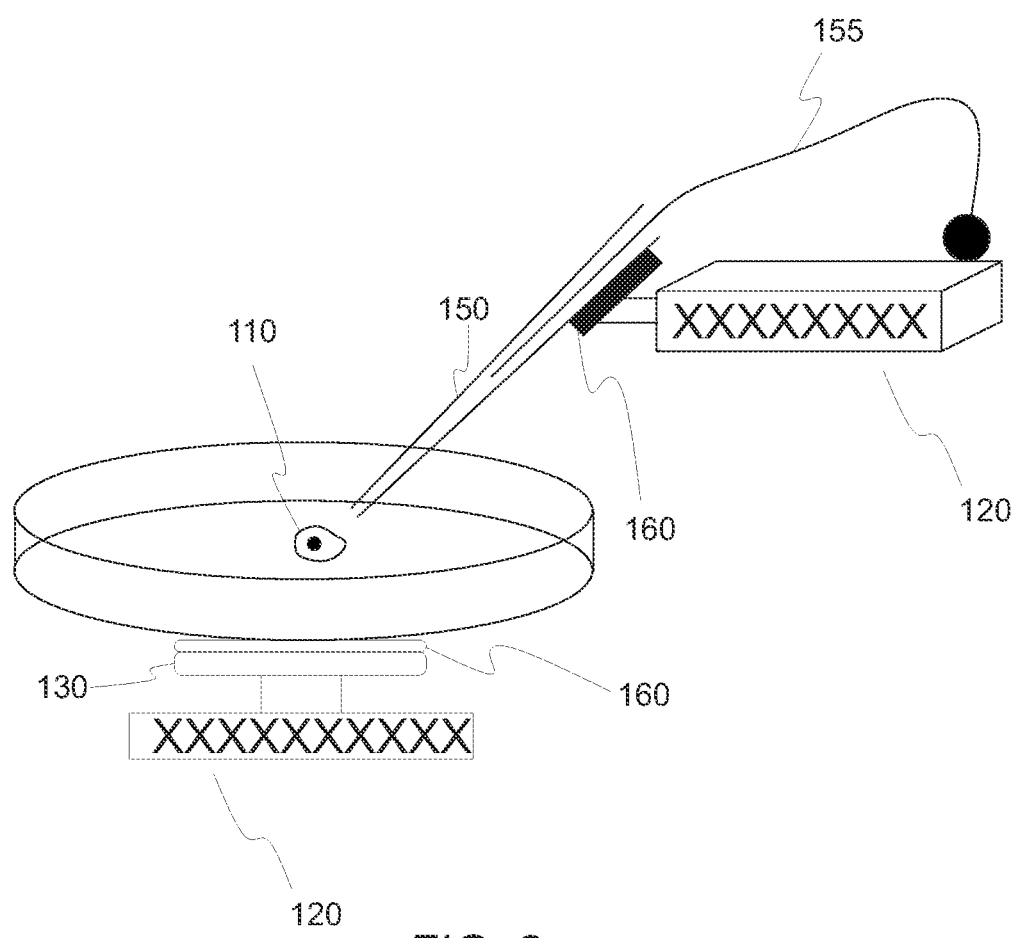
FIG. 2 shows an example of a measurement arrangement where the sensor is held stationary and the target is moved in micromechanical fashion.

FIG. 2 shows an example of a measurement arrangement where the sensor 150 is held stationary and the target 110 is moved in micromechanical fashion. The measurement device 120 may move the sensor or the target in multiple directions. For example, the sensor may be stationary, i.e. not moving, and the target may be moved. The movement may be measured and controlled based on the measurement. The target may be on a petri dish or some other suitable bed settled on a sample holder. The target may be mechanically coupled with the actuator 130. For example, the target may lie on top of the actuator, or it may be mechanically connected to the actuator, for example with the help of a sample holder 160. For example, a sample holder 160 may be screwed or glued to the actuator, and the sample holder 160 may have means for holding the target. The actuator 130 and/or the micromechanical positioning device may be connected to or may be part of a microscope table, a sample holder or other equipment.

The complete micromechanical positioning device may also be arranged to move with respect to a target. For example, the device may be installed on tracks or wheels or other means to move the positioning device. For example, the device may be arranged to move on top of a surface to be measured or tested, such as on top of biological tissue, or on top of a materials surface to be tested.

The positioning device may also comprise a plurality of actuators that are arranged to move with respect to the target and with respect to each other. That is, both the sensor(s) and the sample may be arranged to be movable with respect to each other.

Figure 3:
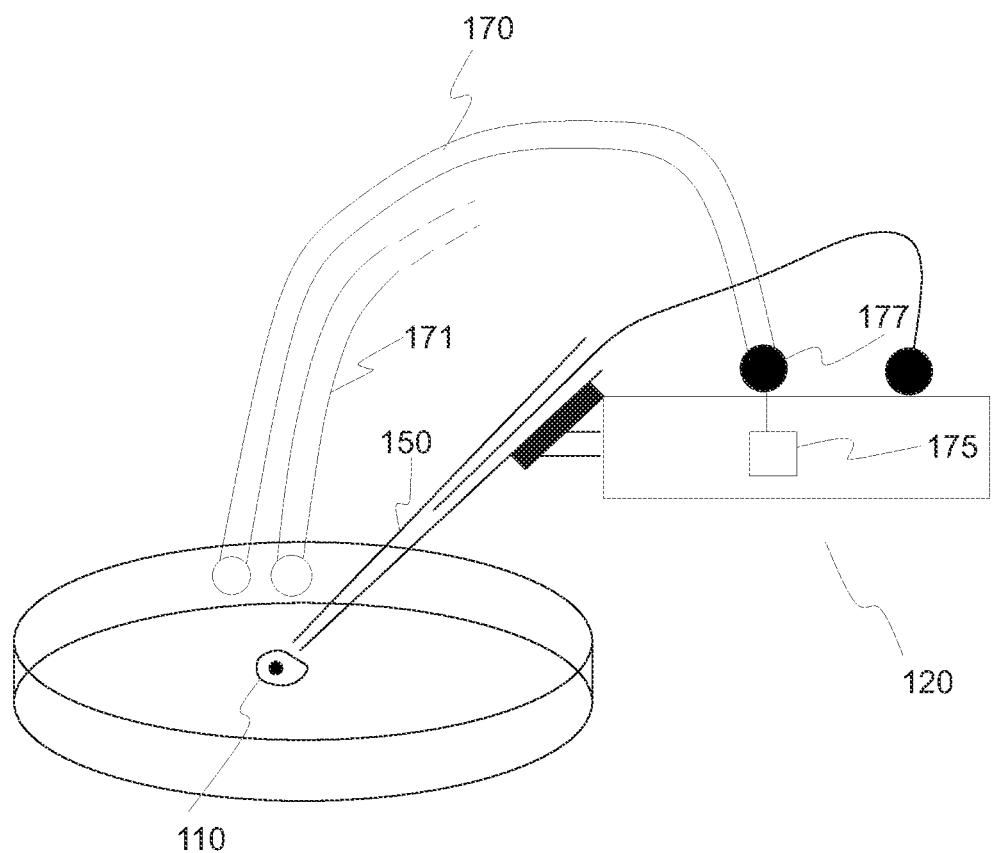
FIG. 3 shows an example of a measurement where an electrical measurement module also includes means for optical measurements and/or stimulation.

FIG. 3. shows an example of a measurement where the measurement device comprises means for optical measurements and/or stimulation. For example, an optic fibre 170 may be integrated to the measurement sensor 150, which connects to the measurement module 175 through an interface 177, and enables stimulating it optically for example by coupling a laser or LED light source or another light source to the back-end of the fiber. It may be possible to measure intensity of fluorescence signal from the target 110 after optical stimulation by coupling the back end of the fiber to suitable detector such as photodiode or photomultiplier, or using another fibre. It is also possible to use a bundle of optical fibers 170, 171 that enables measuring images with many measurement points from the target 110. Instead of optical fiber the optical measurement and stimulation may be implemented with any other type of optical device such as miniature microscope. Electrical measurement and stimulation may be combined with optical measurement and stimulation in any combinations and optical signals can be used in similar way as electrical signals for controlling sensor 150 and/or target 110 position based on the measured information.

The sensor 150 may also be a probe and a force sensor, and correspondingly the read-out electronics may be adapted for the type of sensor, or a sensor for sensing chemical environment, for example pH level, or any other sensor that is suitable to measure physical signal of interest and convey that information to the integrated positioning apparatus.

The measurement device may also comprise a source of physical stimulation source that is relevant to specific test, for example to inject liquid or particles to target, to expose target to physical forces or pressure or any other format of physical or chemical stimulation.

Figure 4A:
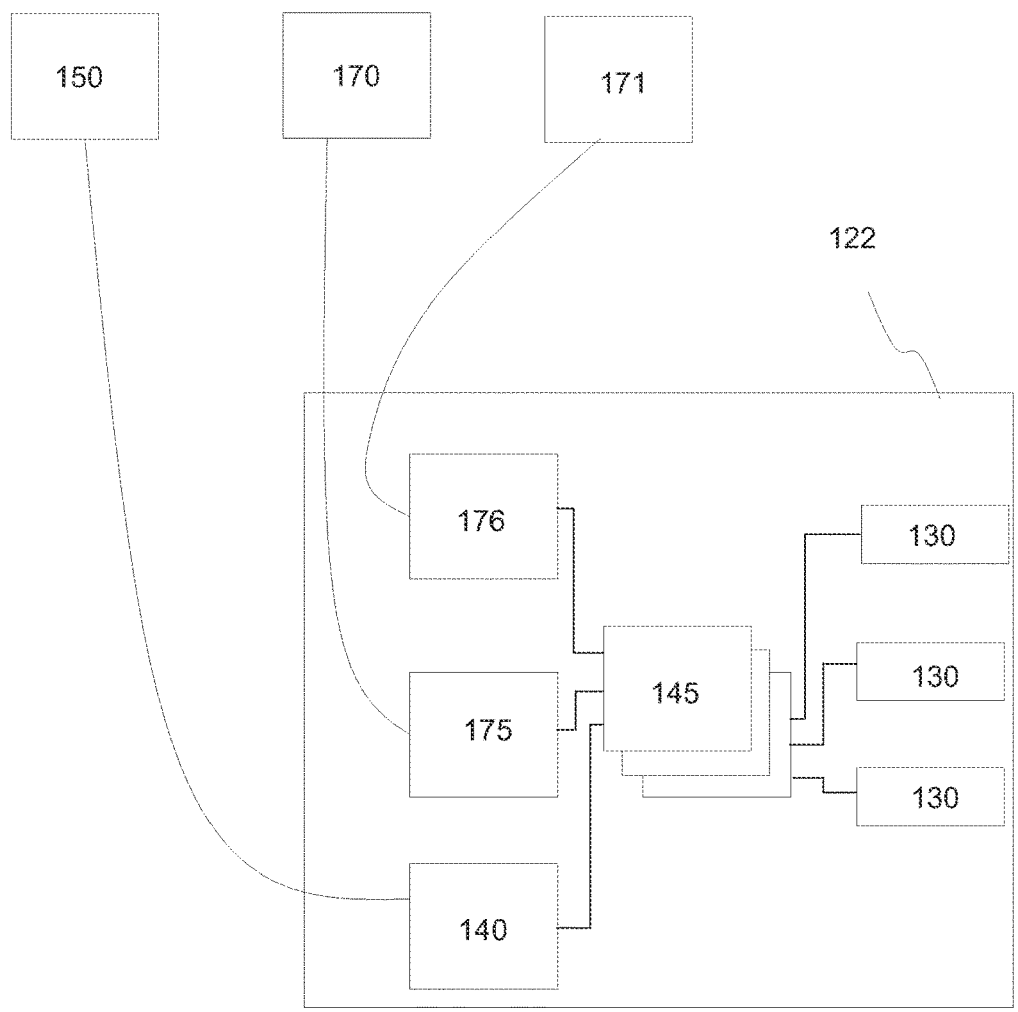
FIGS. 4a and 4b
show example schematic representations of an integrated positioning apparatus with electrical and/or optical measurement and/or stimulation capabilities.

FIG. 4*a* shows an example schematic representation of connections of an integrated positioning apparatus with electrical and/or optical measurement and/or stimulation capabilities. The apparatus may comprise or be connected to various sensors 150, 170, 171, as presented earlier. Various type of probes/sensors may be attached to the apparatus that are suitable of doing various type of electrical and/or optical measurements, such as microelectrodes or probes; electrical measurement may include means to compensate for the electrical characteristics or the probe and target, such as compensate for the probe capacitance or some optical characteristics of the optical measurement probe or target.

The sensors may be connected to their respective sensor read-out electronics 140, 175 and 176 as described earlier, or the read-out electronics may be a single unit receiving a plurality of sensor inputs. For example, the sensor read-out electronics may comprise integrated chip amplifiers for recording signals from living cells with one or more channels. The read-out electronics may also comprise a stimulator or current-supply element for providing voltage, current and/or light to the target being measured. That is, in addition to electrical measurement it may also be possible to control electrical characteristics of the target, i.e. control its voltage and/or inject current while doing electrical measurements. Also, in addition to optical measurement it may also be possible to stimulate target optically and combine this stimulation with electrical and/or optical measurements to measure the stimulation response. In an analogous manner to electrical stimulation, injection of current may also be used to program permanent fuses on semiconductor circuits (setting bits to 0/1 on the chip). Also other kinds of measurements and stimulations may be applied, as has been described earlier.

The positioning apparatus may comprise integrated means of measuring electrical and/or optical signals, comprising measuring voltage and current or doing optical measurements such as intensity or wavelength. Integration may be understood as the measurement being directly connected to the positioning controller (controller for the micromechanical actuator(s)) that is integrated in the apparatus. The positioning controller may be arranged to receive instructions from an external control unit such that these instructions are used in the controlling of the positioning as the logic or parameters for the measured sensor input.

The output of the read-out unit(s) is connected to the manipulator positioning controller(s) 145 for controlling the positioning, e.g. doing closed loop positioning based on measured signals. Both the read-out electronics and the controller may provide their data out through a data output so that they can be saved, that is measured signals and positioning signals may be provided. Information from the measured signals in one manipulator may be also be used to control other manipulators for synchronous positioning.

The positioning device may be integrated in a contiguous structure 122. This may provide the advantage of electrical shielding. Furthermore, as the measuring and position control are closely integrated, delays may be avoided, thus enabling more accurate and faster positioning. Also, the size of the device may thereby be small enough e.g. to fit under a microscope lens and/or to enable access to the sample from almost horizontal direction.

Electrical measurements may be carried out at the read-out electronics by using an amplifier that comprises means to process electrical signals suitable to be transferred directly to the actuator controller (A/D conversion done at the actuator controller). Alternatively, the A/D conversion and, for example, conversion to serial bus format may happen at the read-out electronics, that is, before the actuator controller. Optical measurement may be based on using fiber optic probe or other optical arrangements to detect optical signals from target, and the read-out electronics detects and transforms the measured signal to electronic format for providing it to the actuator controller.

Figure 4B:
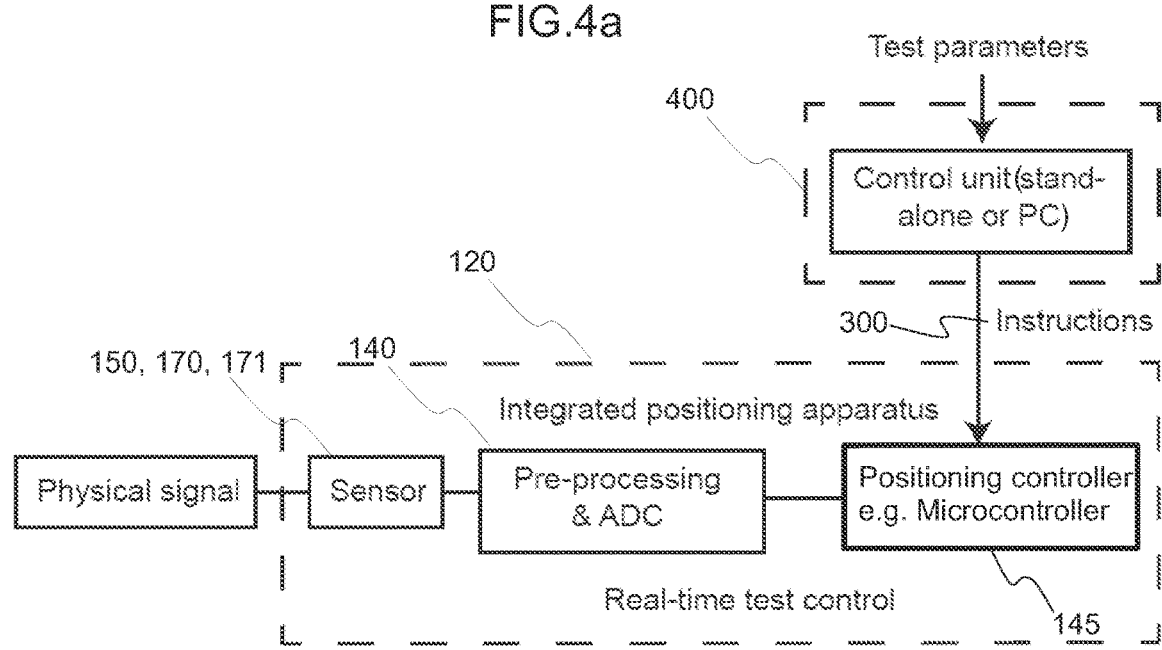

FIG. 4*b* illustrates the functional units of an exemplary measurement and positioning system. The measurement and positioning device may have integrated means to measure physical signals from a sensor 150, 170, 171 with the help of a pre-processing and analog-to-digital converter 140 and to use information from those signals for integrated real-time test control based on instructions from external control unit 400. That is, an external control unit 400 does not need to perform closed loop test control. Instead, the control unit 400 may provide instructions 300 to positioning controller 145 of integrated positioning apparatus 120 on what to do with the measured sensor information. The instructions 300 can vary a great deal e.g. from individual parameters to a set of parameters and/or script language instructions or executable computer code, or any combination of these. For example, the positioning controller may be a microcontroller-based element, and the control unit 400 may provide code and parameters as instructions 300 to the microcontroller. The measurement and positioning system 120 may be at least partly embodied in a casing 122.

For example, in a microelectronic probing application example instructions 300 may be to "approach target whose coordinates are known with some accuracy by moving the probe in a scanning fashion until resistance measured electrically in real time reduces below certain threshold that signals physical contact and then stop moving". For example accuracy of coordinates may be from few micrometers to few tens and hundreds of micrometers and positioning resolution during scanning may be in range from few nanometers to few tens and hundreds of nanometers. Real time may for example mean delays in the closed loop control that few tens or few hundreds of microseconds. Another version is to "measure in parallel the capacitance when approaching the target, reduce speed when the capacitance increases (the capacitance increases when close to target) and stop when a predetermined reduction in resistivity is detected". The small delays achieved by this closed loop test control may enable faster probing and may prevent crashing the probe to target.

Another example for instructions 300 in biological tests may be automated patch clamp experiments, such as "load a micropipette (with electrically conducting solution) with positive pressure to help keeping tip clean when moving in tissue, then drive pipette forward in tissue while measuring electrical impedance, stop when impedance increases above a given threshold (signals that pipette tip is touching cell membrane), change to small negative pressure in pipette to stabilize contact forming, start measurement". Another version of instructions 300 could include a rule for measuring impedance intermittently during measurements and correcting pipette tip position if impedance changes. For these applications, there may be an integrated pressure control in the measurement device. Positioning resolution required in implementing this type of instruction may for example be in the range from few nanometers to few tens and hundreds of nanometers or even less than nanometer when correcting the pipette tip position during the measurement, and delays in the closed loop control may need to be from few tens or few hundreds of microseconds.

Another example of instructions 300 for optogenetics experiments may be as follows: "move optical fiber forward in the brain tissue to approach target area known with certain accuracy, simultaneously measuring fluorescence signal while moving forward and stop when signal exceeds given value". A version of instructions 300 could include a rule for adjusting fiber position slightly if measured fluorescence signal base-line changes in certain manner. Measurement and positioning resolution in implementing such instructions may be similar as provided before in example embodiments.

Figure 5:
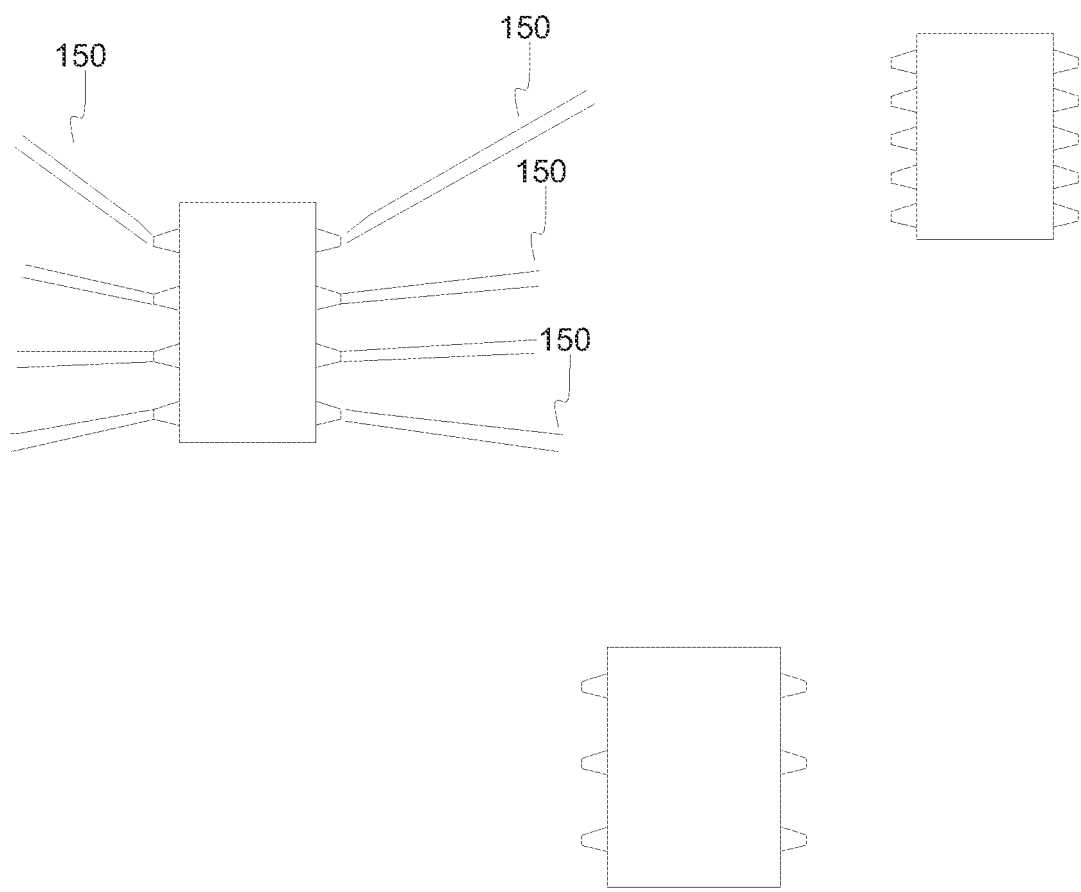
FIG. 5 shows an example where a plurality of simultaneous tests are performed simultaneously.

FIG. 5. shows an example where a plurality of simultaneous tests are performed simultaneously, for example performing electrical tests with two, three, four or more individually controllable sensors at the same time. For example, eight integrated positioning devices with sensors 150 may form a sensor station, which may be used to test microcircuits in automated fashion. A computer may control the sensor station positions in a macroscopic manner and conduct electrical tests in automated fashion based on the microcircuit design layout. Sensor station may be subsequently and automatically moved from one test location to another based on test pad coordinates, and tests are performed and measured information saved to computer or internet based service. The sensors 150 in the sensor station may be positioned accurately in a micromechanical manner by actuators 130 (not shown in FIG. 5).

Each positioning device may be able to carry out a plurality electrical and/or optical measurements simultaneously, i.e. do multichannel measurements using multichannel probes and multichannel measurement heads.

A system for measurement and micromechanical positioning may comprise one or more of positioning devices 120 that are connected to a positioning controller or computer and/or to each other's.

Figure 6:
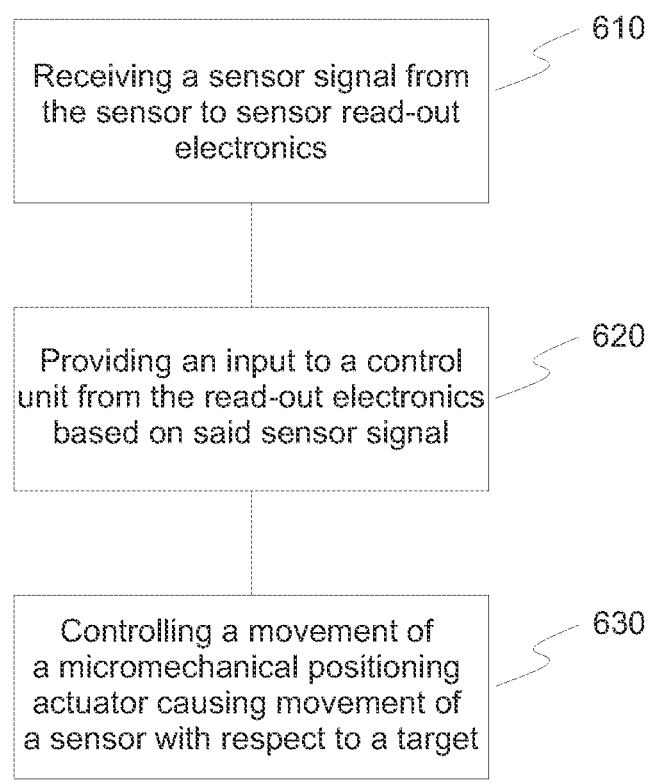
FIG. 6 shows an example flow chart for controlling a measurement device.

FIG. 6 shows an example flow chart for a method for controlling a measurement device. In phase 610, a sensor signal is received from sensor 150 to sensor read-out electronics 140. In phase 620, an input is provided to a positioning controller 145 from the read-out electronics 140 based on the sensor signal. The positioning controller 145 and said read-out electronics 140 may be integrated in a module as a contiguous structure, and therefore the signal may be provided e.g. inside an electrically shielding chassis/enclosure. In phase 630, based on the input, movement of a micromechanical positioning actuator is controlled. The actuator causes movement of a sensor with respect to a target (either by moving the sensor or the target or both).

The measurement device may receive instructions 300 from a control unit for carrying out positioning control with the positioning controller 145. These instructions 300 may be formed as a computer program product embodied on a non-transitory computer-readable medium, where the computer program product comprises positioning control instructions that, when operated on by a processor, cause the measurement and micromechanical positioning device to receive a sensor signal as an input to a positioning controller, control a movement of a micromechanical positioning actuator, causing movement of a sensor with respect to a target by using said positioning control instructions in determining said movement based on said sensor signal.

The control unit 400 may have a computer program comprising computer code that, when operated on by a processor, cause a control unit of a measurement and positioning system to receive user input from a user for controlling a measurement, determine positioning control instructions 300 based on said received user input, said positioning control instructions 300 comprising computer-readable instructions suitable for use by a positioning controller of a measurement device in controlling movement of a micromechanical positioning actuator based on a sensor signal, and provide said positioning control instructions to at least one measurement device of said measurement and positioning system.

The measurement and positioning devices described here may have various application areas. For example, the measurement device may be used in materials testing and fault analysis, production and quality control automation applications, measurements of electrical circuits, biomedical diagnostics and drug development measurements of living cells and any other areas where precise positioning of the measurement sensor is important and where position adjustments based on measured information may be required with small latencies.

The various embodiments of the invention can be implemented with the help of computer program code that resides in a memory and causes the relevant apparatuses to carry out the invention, or with circuitry achieving the same. For example, an integrated positioning apparatus may comprise circuitry and electronics for handling, receiving and transmitting data, computer program code in a memory, and a processor that, when running the computer program code, causes the positioning apparatus to carry out the features of an embodiment. Yet further, a computer may comprise circuitry and electronics for handling, receiving and transmitting data, computer program code in a memory, and a processor that, when running the computer program code, causes the computer to carry out the features of an embodiment.

The various embodiments of the invention can in addition be implemented with the help of an integrated measurement and positioning apparatus comprising the relevant characteristics to carry out the invention, or with devices achieving the same. For example, a mechanical precision instrument may comprise mechanical parts, electrical circuits or components and programmable elements or devices that, when operating the instrument, causes the devices to carry out the features of an embodiment.

The various embodiments of the invention can be further implemented with the help of an electronic circuit comprising the relevant apparatuses to carry out the invention, or with devices achieving the same. For example, an external control device connected via a command port or an interface may cause a positioning controller to carry out the features of an embodiment. Further, an electronic circuit may comprise tools for handling, receiving and transmitting data. The circuit may contain a processor and a program code in a memory, that, when operating, causes the instrument to carry out the features of an embodiment.

It is clear that the present invention is not limited solely to the above-presented embodiments, but it can be modified within the scope of the appended claims.

The invention claimed is:

1. A measurement device for performing measurements using an external sensor, said sensor being positioned related to an external target in micromechanical fashion, said measurement device comprising:
 a body;
 a micromechanical positioning actuator for causing movement of said sensor with respect to said target;
 a positioning controller embodied within said body, said positioning controller having a sensor input coupled to said sensor, said sensor input arranged to receive a sensor signal from said sensor to said positioning controller; and
 said positioning controller having an output, said output coupled to said micromechanical positioning actuator for controlling said movement based on said sensor signal;
 sensor read-out electronics for producing said sensor signal, wherein said sensor read-out electronics is embodied within said body and is coupled to said sensor and to said sensor input of said
 positioning controller, and wherein the micromechanical positioning actuator, the positioning controller and the sensor read-out electronics are integrated in the body as a physically contiguous structure,
 wherein the sensor is externally integrated to said body of the measurement device.

2. The measurement device according to claim 1, further comprising memory for storing positioning control instructions, wherein said positioning control instructions comprise computer-readable instructions suitable for use by said positioning controller in controlling said movement based on said sensor signal, wherein said positioning controller is arranged to control said movement based on said sensor signal and said positioning control instructions.

3. The measurement device according to claim 2, further comprising an instruction input for receiving said positioning control instructions to said memory from a source external to said measurement device.

4. The measurement device according to claim 1, wherein said sensor is an electrical sensor arranged to detect a voltage, current, conductance, capacitance or other electrical characteristics at said sensor, wherein said sensor read-out electronics comprises at least one of a detector and an amplifier for detecting or amplifying said electrical characteristics.

5. The measurement device according to claim 4, wherein said amplifier comprises at least one operational amplifier and a resistive, capacitive or transistor-based feedback path between the output of the operational amplifier and an input of the operational amplifier.

6. The measurement device according to claim 1, further comprising a patch-clamp sensor for measuring bioelectric signals.

7. The measurement device according to claim 1, wherein said sensor is an optical sensor and said sensor read-out electronics comprises an optical-to-electric converter coupled to said optical sensor and said sensor input of said positioning controller.

8. The measurement device according to claim 7, further comprising an image processor.

9. The measurement device according to claim 1, wherein said sensor comprises a sensor for sensing a physical quantity, for example, force sensor, voltage sensor, current sensor or capacitance sensor.

10. The measurement device according to claim 1, wherein said sensor is a sensor for sensing chemical environment, for example, a pH level sensor.

11. The measurement device according to claim 1, comprising: at least one further sensors; at least one micromanipulator actuator for causing movement of said at least one further sensor with respect to said target; said positioning controller having at least one further sensor input coupled to said at least one further sensor, said at least one further sensor input arranged to receive further sensor signals from said at least one further sensor to said positioning controller; and said positioning controller arranged to control said movement based on said further sensor signals.

12. The measurement device according to claim 1, further comprising at least one of a direct or alternate current and voltage source for controlling voltage of at least one of said target and injecting current to said target during measurement.

13. The measurement device according to claim 1, further comprising a source of electromagnetic radiation for feeding said radiation to said target, wherein said electromagnetic radiation comprises at least one of visible light, infrared and ultraviolet radiation suitable for stimulating a living biological target, or x-ray radiation.

14. The measurement device according to claim 1, further comprising: a stimulator for stimulating the target, wherein said stimulating comprises at least one from the group of controlling voltage, injecting current, applying magnetic field, injecting liquid, injecting particles controlling pressure, stretching, pushing or pulling, other physical stimulation and chemical stimulation.

15. The measurement device according to claim 1, wherein said positioning controller is arranged to control said movement of said sensor with respect to said target in a closed-loop control, such that said sensor signal from said read-out electronics is maintained essentially according to characteristics defined in the instructions or movement is stopped at a condition defined by the position control instructions.

16. A control unit for controlling a measurement and positioning system, comprising:
   an interface for receiving user input from a user for controlling a measurement;
   a processor and a memory;
   computer program code in said memory, said code arranged to, when executed on said processor,
   cause said control unit to determine positioning control instructions based on said received user input,
   said positioning control instructions comprising computer-readable instructions suitable for use by a positioning controller of a measurement device in controlling movement of a micromechanical positioning actuator based on an external sensor signal to position said sensor related to an external target, said sensor signal received from said sensor to a sensor input of said positioning controller; and
   an instruction interface for providing said positioning control instructions to at least one measurement device of said measurement and positioning system, wherein the sensor is externally integrated to a body of the measurement device.

17. The measurement system comprising a plurality of devices according to claim 1 and the control unit according to claim 16, the control unit being coupled to one or more of said plurality of devices for providing positioning control instructions to said one or more of said plurality of devices.

18. A method for performing measurements by a measurement device using an external sensor, said sensor being positioned related to an external target in micromechanical fashion, the method comprising:
   receiving a sensor signal from said sensor to sensor read-out electronics;
   providing a sensor input to a positioning controller from said read-out electronics based on said sensor signal, said positioning controller and said read-out electronics being integrated in a body as a physically continuous structure; and
   based on said sensor input, controlling by said positioning controller a movement of a micromechanical positioning actuator causing movement of the sensor with respect to said target,
   wherein the micromechanical positioning actuator is also integrated in the body as a physically continuous structure, wherein the sensor is externally integrated to said body of the measurement device.

19. The method according to claim 18, further comprising: receiving positioning control instructions from a source external to said measurement device, said positioning control instructions comprising computer-readable instructions suitable for use by said positioning controller in controlling said movement based on said sensor signal;
   storing said positioning control instructions in a memory; and controlling said movement by said positioning controller based on said sensor input and said positioning control instructions.

20. A computer program product embodied on a non-transitory computer-readable medium, wherein said computer program product comprises positioning control instructions that, when operated on by a processor, cause a micromechanical positioning device to carry out the method according to claim 18.

21. A computer program product embodied on a non-transitory computer-readable medium, wherein said computer program product comprises computer code that, when operated on by a processor, cause a control unit of a measurement and positioning system to:
   receive user input from a user for controlling a measurement;
   determine positioning control instructions based on said received user input, said positioning control instructions comprising computer-readable instructions suitable for use by a positioning controller of a measurement device in controlling movement of a micromechanical positioning actuator based on an external sensor signal to position said sensor related to an external target, said sensor signal received from said sensor to a sensor input of said positioning controller; and
   provide said positioning control instructions to at least one measurement device of said measurement and positioning system, wherein the sensor is externally integrated to a body of the measurement device.

* * * * *